(12) United States Patent
Hofer-Kraner et al.

(10) Patent No.: US 10,401,651 B2
(45) Date of Patent: Sep. 3, 2019

(54) PROTECTION DEVICE

(71) Applicant: Optrel Holding AG, Appenzell (CH)

(72) Inventors: Ramon Hofer-Kraner, Herisau (CH);
Jonathan Heusser, Uerikon (CH);
Daniel Blöchlinger, Gallenkappel (CH)

(73) Assignee: Optrel Holding AG, Appenzell (CH)

( * ) Notice: Subject to any disclaimer, the term of this patent is extended or adjusted under 35 U.S.C. 154(b) by 0 days.

(21) Appl. No.: 15/447,963

(22) Filed: Mar. 2, 2017

(65) Prior Publication Data

US 2017/0255027 A1 Sep. 7, 2017

(30) Foreign Application Priority Data

Mar. 3, 2016 (EP) ..................................... 16158451

(51) Int. Cl.
*G02C 7/10* (2006.01)
*A61F 9/06* (2006.01)
*G02C 5/12* (2006.01)

(52) U.S. Cl.
CPC ............... *G02C 7/101* (2013.01); *A61F 9/06* (2013.01); *A61F 9/067* (2013.01); *G02C 5/122* (2013.01); *A61F 2250/0008* (2013.01)

(58) Field of Classification Search
CPC ......... G02C 7/101; G02C 5/122; A61F 9/067; A61F 9/06; A61F 2250/0008
USPC ................... 351/44, 47, 48, 159.6; 2/8.2–8.8
See application file for complete search history.

(56) References Cited

U.S. PATENT DOCUMENTS

| | | | | | |
|---|---|---|---|---|---|
| 1,835,792 | A | * | 12/1931 | Lum ...................... | H04M 1/05 379/430 |
| 1,885,426 | A | * | 11/1932 | Flood ...................... | A61F 9/06 2/8.2 |
| 2,353,043 | A | * | 7/1944 | Kraski et al. ............. | A61F 9/06 2/8.1 |
| 2,668,341 | A | * | 2/1954 | Arzt ...................... | A44C 7/006 24/499 |
| 2,761,145 | A | * | 9/1956 | Malcom, Jr. ............ | A61F 9/025 2/445 |

(Continued)

FOREIGN PATENT DOCUMENTS

| DE | 10 2006 048 204 A1 | 9/2007 |
|---|---|---|
| EP | 2 839 817 A1 | 2/2015 |
| EP | 3 000 447 A1 | 3/2016 |

OTHER PUBLICATIONS

Extended European Search Report dated Aug. 12, 2016 issued in corresponding EP patent application No. 16158451.1 (and partial English translation).

*Primary Examiner* — George G King (74) *Attorney, Agent, or Firm* — Posz Law Group, PLC (57) ABSTRACT

The invention is based on a protection device, in particular a glare-protection device, with at least one optical glare-protection filter comprising a nose cut-out, with at least one sensor unit, which is provided to capture a work state and to control, depending on this, a permeability of the glare-protection filter, with at least one shield unit, in which the at least one glare-protection filter is fixedly accommodated, and with at least one head-fastening unit for a fastening to a user's head. It is proposed that the protection device comprises at least one adjusting unit, by which a position of the at least one shield unit is implemented in such a way that it is movable with respect to the at least one head-fastening unit in a defined manner.

9 Claims, 9 Drawing Sheets

(56) References Cited

U.S. PATENT DOCUMENTS

| | | | |
|---|---|---|---|
| 4,708,034 A * | 11/1987 | Oetiker | B25B 7/00 |
| | | | 81/9.3 |
| 5,208,688 A * | 5/1993 | Fergason | A61F 9/067 |
| | | | 349/104 |
| 9,629,752 B1 * | 4/2017 | Graham | A61F 9/067 |
| 2007/0220649 A1 | 9/2007 | Huh | |
| 2008/0060102 A1 | 3/2008 | Matthews et al. | |
| 2011/0179541 A1 | 7/2011 | Wright | |

* cited by examiner

PROTECTION DEVICE

CROSS REFERENCE TO RELATED APPLICATION

This application is based on and incorporates herein by reference European Patent Application No. 16158451.1 filed on Mar. 3, 2016.

STATE OF THE ART

The invention relates to a protection device, in particular a glare-protection device.

From EP 2 839 817 A1 a protection device is already known, with at least one optical glare-protection filter comprising a nose cut-out, with at least one sensor unit, which is provided to capture a work state and to control, depending on this, a permeability of the glare-protection filter, with at least one shield unit, in which the at least one glare-protection filter is fixedly accommodated, and with at least one head-fastening unit for fastening to a user's head.

The objective of the invention is in particular to provide a generic device with improved characteristics regarding a user's comfort as well as regarding safety. The objective is achieved, according to the invention, by the features of patent claim 1, while advantageous implementations and further developments of the invention may become apparent from the subclaims.

ADVANTAGES OF THE INVENTION

The invention is based on a protection device, in particular a glare-protection device, with at least one optical glare-protection filter comprising a nose cut-out, with at least one sensor unit, which is provided to capture a work state and to control, depending on this, a permeability, in particular a light permeability, of the glare-protection filter, with at least one shield unit, in which the at least one glare-protection filter is fixedly accommodated, and with at least one head-fastening unit for a fastening to a user's head. Preferably the glare-protection filter is accommodated in the shield unit fixedly as regards its position.

It is proposed that the protection device comprises at least one adjusting unit, by which a position of the at least one shield unit is implemented in such a way that it is movable with respect to the at least one head-fastening unit in a defined manner. Preferably a position of the at least one shield unit is implemented in such a way that it is movable in a controlled manner with respect to the at least one head-fasting unit by means of the adjusting unit. By a "protection device" is in particular, in this context, a device to be understood which is provided to protect a user from a too high brightness level and/or from sparks. Preferably it is in particular to be understood as a device serving to protect a user's eyes and/or a user's face region during a welding and/or grinding process. Preferentially it is in particular to be understood as a glare-protection device, which in particular serves to protect a user's eyes at least during a welding process. A variety of implementations of a protection device are conceivable which are deemed expedient by someone skilled in the art, e.g. implementations as a welding helmet, a welding visor, a welding mask and/or a welding shield. Furthermore, in this context an "optical glare-protection filter" is to be understood in particular as an optical filter, which in particular implements a protective glass and/or a protective synthetic glass. It is preferentially, in particular, to be understood as an optical filter the light permeability of which is implemented adjustable. Preferably it is in particular to be understood as an optical welding protective filter with an auto-darkening function. Especially preferably the glare-protection filter comprises at least one liquid-crystal layer which is switchable in the transmission. A variety of implementations of the optical glare-protection filter are conceivable which are deemed expedient by someone skilled in the art, among which there is in particular an "ADF" to be understood, which is also denominated an "automatic darkening filter" or an "automatic welder's protection filter". Furthermore, a "nose cut-out" is, in this context, in particular to mean an immaterial recess in an at least partly translucent partial region of the glare-protection filter, which is in at least one operative position of the protection device at least partly provided for at least partly accommodating a user's nose. Preferably the recess is in each point of at least one plane, which is in particular parallel to a main extension plane of the glare-protection filter, in an angle range of at least 180 degrees, encompassed by a material partial region, in particular an at least partly translucent partial region of the glare-protection filter. Preferentially the glare-protection filter extends around a user's nose in at least one operative position. Especially preferentially a vertical extension of the nose cut-out is at least 10%, preferably at least 30%, preferentially at least 50% and particularly preferably at least 55% of a vertical extension of the glare-protection filter. By a "sensor unit" is, in this context, in particular a unit to be understood which is provided to capture at least one parameter and/or physical property, wherein the capturing may take place actively, e.g. in particular by generating and emitting an electrical measuring signal, and/or passively, e.g. in particular by capturing property changes of a sensor component. A variety of sensor units is conceivable which are deemed expedient by someone skilled in the art. Preferably the sensor unit in particular comprises at least one photo cell. Preferentially the photo cell is in particular provided at least to optically detect an electric arc. Furthermore, in this context, a "shield unit" is in particular to be understood as a unit which is in a regular operative position arranged in front of a user's face. Preferably it is in particular to be understood as a unit which, in an operative position of the protection device, in particular shields at least a substantial portion of a user's face. Preferentially it is in particular to be understood as a unit which is provided for protecting a face, e.g. from flying sparks. Preferably the shield unit is in particular provided to form a protective barrier between a work area and a user's face. Furthermore, in this context, a "head-fastening unit" is in particular to be understood as a unit provided for fastening, in particular fixating, the protection device to a user's head. Preferably the unit is herein provided to at least partly engage around the user's head. In this context, "at least partly engage around" is in particular to mean that a head is encompassed by the head-fastening unit in at least one plane, in an angle range of at least 160 degrees, preferably at least 180 degrees, preferentially at least 270 degrees and particularly preferably at least 360 degrees. Especially preferentially the head-fastening unit is in a regular operation state provided to lie at least against a forehead as well as a back of a user's head of. "Provided" is in particular to mean specifically programmed, designed and/or equipped. By an object being provided for a certain function is in particular to be understood that the object fulfills and/or implements said certain function in at least one application state and/or operation state.

Furthermore, in this context, an "adjusting unit" is in particular to be understood as a unit by means of which a position of the at least one shield unit is implemented in such a way that it is adjustable, in particular manually adjustable, with respect to the at least one head-fastening unit in a defined manner. Preferably the adjusting unit comprises at least one adjusting element, via which a user may change a position and/or orientation of the shield unit with respect to the at least one head-fastening unit in a defined manner. Especially preferentially the adjusting unit is in particular provided to at least guide a movement of the at least one shield unit with respect to the at least one head-fastening unit in a defined manner. Principally it is also conceivable that the shield unit is moved directly with respect to the head-fastening unit, wherein a movement is, in particular by the adjusting unit, in a defined manner. "In a defined manner" is herein in particular to mean that a movement of the shield unit is guided. Preferably it is also to mean that a limit of a movement of the shield unit with respect to the at least one head-fastening unit is given by the adjusting unit. Particularly preferably it is in particular to mean that the shield unit is fixable, in particular lockable, in a plurality of positions with respect to the at least one head-fastening unit, in particular within the limits of movability.

By means of the protection device according to the invention, in particular an advantageously variable adjustment of a position of the shield unit is achievable. It is in particular achievable that the shield unit may be positioned in a user-specifically optimum manner. This preferably allows implementing the optical glare-protection filter advantageously small and/or implementing a field of vision advantageously great. In this way in particular an advantageously high level of user comfort is achievable. With a great field of vision, in particular a high level of safety may be also ensured. Moreover, by the optimum adjustment of a position of the shield unit a high level of safety is achievable.

It is also proposed that a position of the at least one shield unit is implemented in such a way that it is fixable by the at least one adjusting unit in at least two adjustments with respect to the at least one head-fastening unit. Preferably a position of the at least one shield unit is lockable, via the at least one adjusting unit, in at least two differing adjustments with respect to the at least one head-fastening unit. Preferentially the at least one shield unit is fixable, in particular lockable, in particular in an intended operative position. Especially preferentially the at least one shield unit is lockable, via the at least one adjusting unit, within the limits of movability, in any required position and/or adjustment, in particular operative adjustment, with respect to the at least one head-fastening unit. "Fixable" is in particular to mean, in this context, that a relative position of the shield unit is implemented in such a way that it is fixable respectively lockable, in particular manually fixable respectively lockable. Preferably by a fixation in particular inadvertent changing a position and/or orientation of the shield unit, caused in particular just by the weight force of the shield unit itself, may be avoided, particularly preferably even in case of an impact of a force which is at least twice as great as a weight force of the shield unit. Especially preferentially an alignment and/or position and orientation of the shield unit is fixable, wherein a mere pivot movement, in particular for removing the shield unit out of a region in front of a user's face, is effected in particular independently from this. In this way in particular an advantageously variable adjustment of a position of the shield unit is achievable. Preferably it is in this way achievable that the shield unit may be positioned in a user-specifically optimum manner. By optimally adjusting a position of the shield unit, in particular an advantageously great field of vision is achievable. This further allows, in particular, avoiding a change of position of the shield unit. As a result of this, it is in particular also possible to adapt the protection device to a shape of a user's head individually.

Beyond this it is proposed that a position of the at least one shield unit is implemented in such a way that it is fixable by the at least one adjusting unit in at least two operative adjustments with respect to the at least one head-fastening unit. In this context, an "operative adjustment" is in particular to mean an adjustment of the shield unit in which the shield unit carries out and/or is able to carry out an intended protective function. It is preferentially to mean in particular an adjustment wherein the shield unit is arranged in front of a user's face. Especially preferentially the at least two fixable operative adjustments differ in particular by a distance between the optical glare-protection filter and the user's eyes, and/or by an angle between the shield unit and the head-fastening unit, and/or by a height level at which the optical glare-protection filter is arranged with respect to the user's head. As a result of this, a user may preferably choose between at least two operative adjustments. This in particular allows achieving an advantageously high degree of operative comfort. Preferably, with the protection device a user may choose whether the shield unit is to lie upon a user's nose or is to be spaced apart from the user's nose. In particular, this allows changing between an arrangement for spectacle wearers and an arrangement for users without spectacles. Users without spectacles may in this way achieve an optimum field of vision, whereas spectacle wearers obtain an advantageous wearing comfort.

It is moreover proposed that a direct distance between the user's eyes and the optical glare-protection filter is implemented in such a way that it is adjustable by the at least one adjusting unit. Preferably a distance between the user's eyes and the optical glare-protection filter is adjustable, in operation, perpendicularly to a head axis via the at least one adjusting unit. Preferentially a distance between the user's eyes and the optical glare-protection filter is adjustable, in operation, approximately perpendicularly to a main extension plane of the glare-protection filter via the at least one adjusting unit. In this context, a "direct distance" is in particular to mean a distance between the user's eyes and the optical glare-protection filter during operation, and thus with direct eye contact. In this way in particular advantageously variable adjusting of a position of the shield unit is achievable. Preferably it is in this way achievable that the shield unit may be positioned in a user-specifically optimum manner. Depending on a welder's head circumference and well-being, in this way advantageously the longitudinal position of the optical glare-protection filter is adjustable. Moreover, in this way a longitudinal position of the optical glare-protection filter may be optimally adapted for spectacle wearers as well. The nearer to the face the optical glare-protection filter is arranged, the greater will the field of vision be for the user.

Further it is proposed that a height and/or an angle of the at least one shield unit is in an operative adjustment implemented in such a way that it is adjustable by the at least one adjusting unit with respect to the at least one head-fastening unit. Preferably a height and/or an angle of the at least one shield unit are/is implemented in such a way that they are/it is adjustable in particular in a plane that is parallel to a head axis as well as perpendicular to a main extension plane of the optical glare-protection filter. As a result of this, in particular an advantageously variable adjustment of a position and/or orientation of the shield unit is achievable. Preferentially this allows in particular achieving in particular a positioning of the shield unit in a user-specifically optimum manner. By means of the optimum adjustment of a position of the shield unit, in particular an advantageously great field of vision is achievable.

It is also proposed that the at least one shield unit comprises at least one face abutment, which is provided to contact a user's face in an end position of the shield unit. By a "face abutment" is, in this context, in particular an abutment to be understood which is provided to contact a user's face for the purpose of defining an end position of the shield unit with respect to a user's face. It is preferentially to be understood, in particular, as an abutment the end position of which depends on a shape of a user's face. Particularly preferably it is in particular to be understood as an abutment in which an abutment position is defined by a contact between a face and a face abutment. In this way, an end position of the shield unit is definable in a reliable manner. Furthermore, in this way the shield unit may be brought into an operative position in a reliable manner. In particular, this allows achieving an optimum position of the shield unit with respect to a user's face. Preferably a face-specific abutment may be provided.

Moreover it is proposed that the at least one face abutment is embodied by a nosepiece, which is in at least one operative adjustment provided to contact a user's nose. Preferably the nosepiece is in at least one operative position provided to contact a bridge of a user's nose. Preferably the nosepiece is in at least one operative position provided to contact a nasal pyramid of a user's nose. Especially preferentially the nosepiece is implemented by a spectacle-like nosepiece. Preferably the nosepiece comprises at least one nose pad. Preferentially the nosepiece comprises at least two nose pads. Especially preferentially a position and/or orientation of the nose pads are/is adjustable. The nosepiece is in particular adaptable to a shape of a nose. This allows reliably defining an end position of the shield unit. In particular, as a result of this an optimum positioning of the shield unit is achievable with respect to a user's face. Preferably a position of the shield unit may be aligned with respect to a center of a face. A reliable positioning of the shield unit is achievable with respect to the user's eyes. Moreover at least a small portion of a weight of the protection device may be supported on the nose. This allows in particular avoiding the protection device sliding downwards during operation.

It is further proposed that the at least one face abutment of the at least one shield unit is provided for a positioning of the at least one shield unit with respect to a user's face. This allows achieving a reliable positioning of the shield unit in an end position. This also allows achieving an optimum positioning of the shield unit with respect to a user's face, in particular to the user's eyes. A position of the shield unit may furthermore be aligned with respect to a center of a face. In particular, in this way slipping during operation may be avoided.

Moreover it is proposed that the head-fastening unit defines, in a regularly worn state, a head axis, with respect to which a main extension plane of the optical glare-protection filter is substantially angled in at least one operative adjustment. Preferably the main extension plane of the optical glare-protection filter is angled downwards with respect to the head axis. By a "head axis" is, in this context, in particular an axis to be understood which is rigid with respect to a head. It is preferably to be understood as an axis extending through a geometric center of the user's head. Preferentially, if the user has an upright posture, the head axis extends in parallel to a main extension direction of the user's rump.

Furthermore, in this context, "substantially angled" is in particular to mean that a smallest angle between the main extension plane of the optical glare-protection filter and the head axis is at least 5 degrees, preferably at least 10 degrees and especially preferentially at least 15 degrees. In this way in particular an advantageous angle of a user's vision onto the optical glare-protection filter is achievable, which is as near to a right angle as possible. In particular, the angling of the optical glare-protection filter may allow a perpendicular view of the user through the optical glare-protection filter, thus lessening the impact which the dependency of the optical glare-protection filter on an angle of vision has on the visual quality. In particular with a natural work posture, in which a user's view is usually slightly inclined downwards, this allows lessening the impact which the dependency of the optical glare-protection filter on an angle of vision has on the visual quality.

It is also proposed that the at least one head-fastening unit is embodied by a head strap. By a "head strap", in this context, in particular a head-fastening is to be understood which comprises at least one band-like element provided to at least partly encompass a user's head. Preferably the head strap is adaptable to a size of a user's head. Preferentially an effective length of the at least one band-like element may be modified for adaptation of the head strap. As a result of this, in particular an especially reliable head-fastening unit may be rendered available. Furthermore this allows providing a particularly lightweight and flexible head-fastening unit.

Beyond this it is proposed that the at least one shield unit is made of an at least substantially non-deformable material. Preferably the at least one shield unit is made of a material having a high elasticity module. A "high elasticity module" is in this context in particular to mean an elasticity module of at least 0.5 kN/mm$^2$, preferably at least 1 kN/mm$^2$ and especially preferentially at least 5 kN/mm$^2$ at a temperature of 20° C. A variety of non-deformable materials are conceivable which are deemed expedient by someone skilled in the art, e.g. in particular plastic, for example polycarbonates, polyamides or the like, or metal. Preferably a "non-deformable material" is in particular to be understood as a material that differs from a textile material. This allows in particular achieving an advantageously high degree of safety of the shield unit. Preferably this allows achieving reliable protection by the shield unit. In particular, an undesired deformation is thus avoidable.

The protection device according to the invention is herein not to be restricted to the application and implementation described above. In particular, the protection device according to the invention may comprise, for fulfilling a functionality herein described, a number of respective elements, components and units that may differ from a number that is mentioned herein.

DRAWINGS

Further advantages may be gathered from the following description of the drawings. The drawings show an exemplary embodiment of the invention. The drawings, the description and the claims contain a plurality of features in combination. Someone skilled in the art will purposefully also consider the features separately and will find further expedient combinations.

It is shown in.

DESCRIPTION OF THE EXEMPLARY EMBODIMENT

Figure 1:
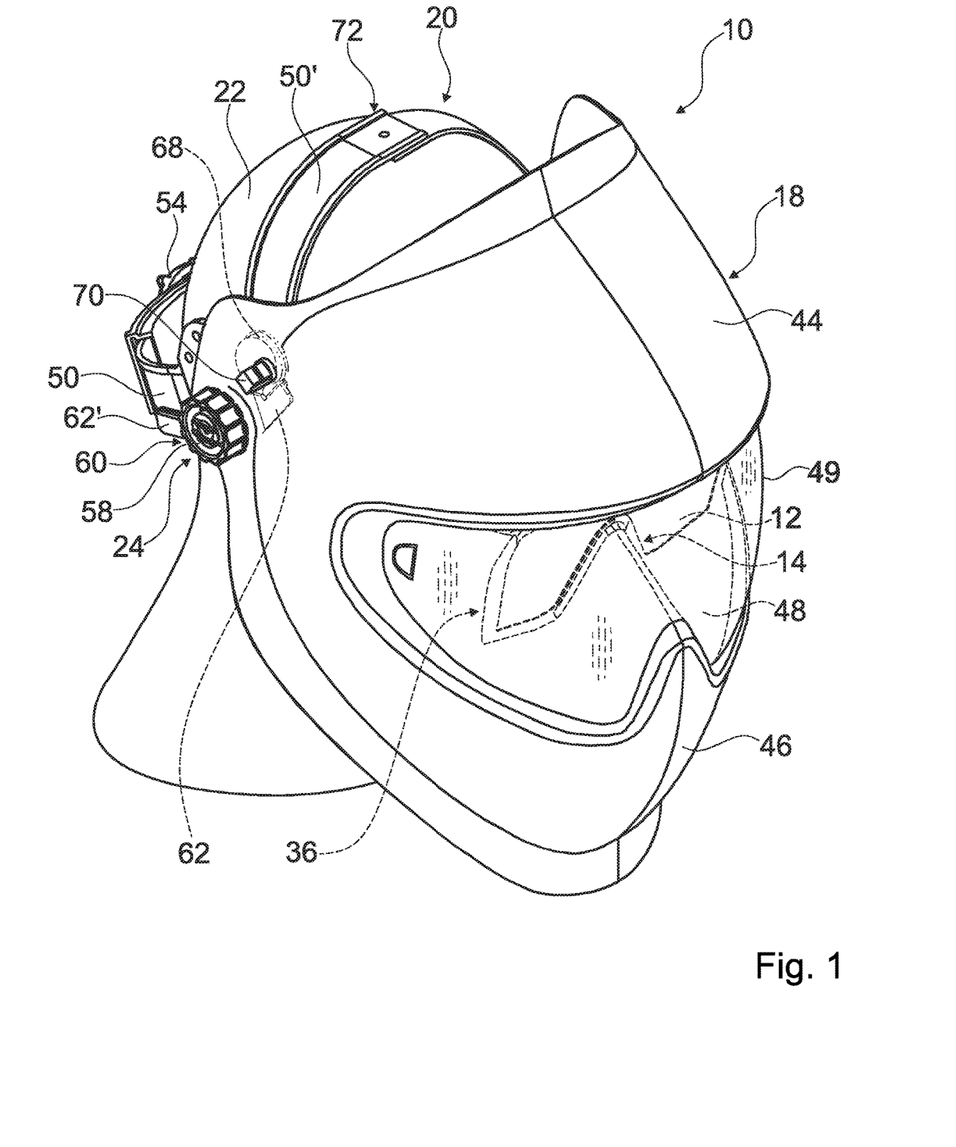
FIG. 1 the protection device according to the invention with a shield unit, with a head-fastening unit, with an optical glare-protection filter and with a front cover plate, on a user's head, in a schematic view, FIG. 2 the protection device according to the invention with the shield unit, with the head-fastening unit and the optical glare-protection filter, in a schematic lateral view, FIG. 3 the protection device according to the invention with the shield unit, with the head-fastening unit and the optical glare-protection filter, without the front cover plate, in a schematic front view, FIG. 4 the head strap unit of the protection device according to the invention, in a schematic lateral view, FIG. 5 the head strap unit of the protection device according to the invention, in a schematic front view, FIG. 6 the shield unit and the front cover plate of the protection device according to the invention, in a schematic lateral view in an exploded presentation, FIG. 7 the optical glare-protection filter of the protection device according to the invention, in a schematic front view, FIG. 8 the protection device according to the invention with the shield unit, with the head-fastening unit and the optical glare-protection filter, in a partly transparent schematic lateral view during adjustment of an eye distance, FIG. 9 the protection device according to the invention with the shield unit, with the head-fastening unit and the optical glare-protection filter, in a partly transparent schematic lateral view during adjustment of an angle, FIG. 10 the protection device according to the invention with the shield unit, with the head-fastening unit and the optical glare-protection filter, in a partly transparent schematic lateral view during adjustment of a height, FIG. 11 fields of vision of the protection device in two different adjustments in comparison to the field of vision of already known welding helmets, in a schematic view, and FIG. 12 a configuration of a measurement of the field of vision of the welding helmets, in a schematic view.

FIG. 1 shows a protection device 10 on a user's head 22. The protection device 10 is provided to be worn by a user on his head 22 during operation. FIG. 1 shows the protection device 10 in an operative position. The protection device 10 is implemented by a welding helmet. Principally, however, another implementation of the protection device 10, deemed expedient by someone skilled in the art, would also be conceivable.

Figure 3:
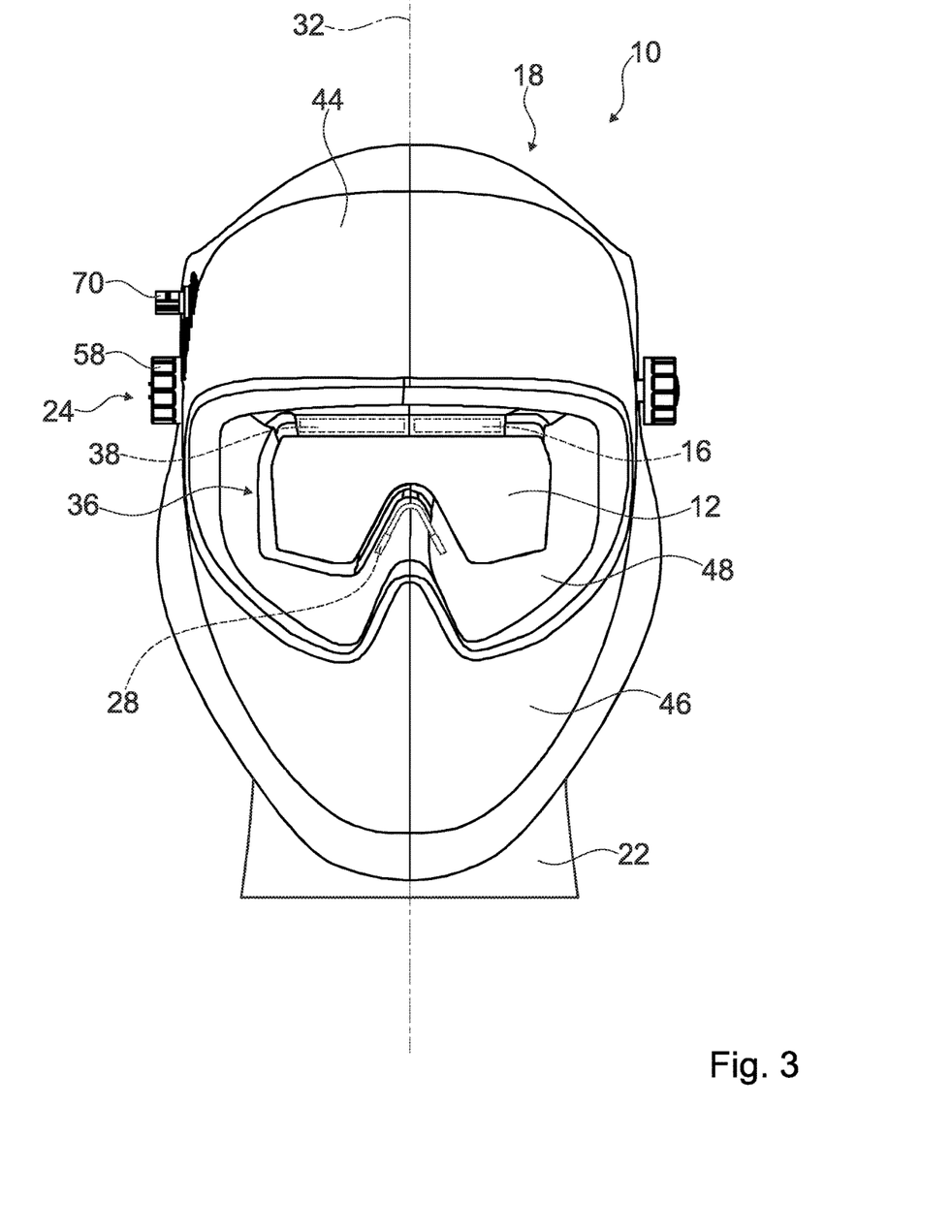
Figure 7:
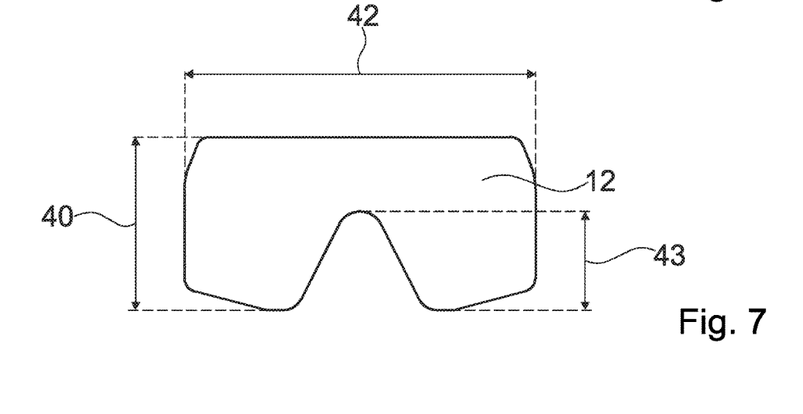

The protection device 10 comprises an optical glare-protection filter 12. Furthermore the protection device 10 comprises a sensor unit 16. The sensor unit 16 is provided to capture work state and to control, depending on this, a permeability of the glare-protection filter 12. The sensor unit 16 comprises at least one sensor which is provided to detect a welding process or an event of a bright light, which could damage or otherwise affect a user's eyes 26. The sensor of the sensor unit 16 is implemented by a photo cell. Principally, however, another implementation of the sensor of the sensor unit 16, deemed expedient by someone skilled in the art, would also be conceivable. The protection device 10 also comprises a protective cassette 36. The optical glare-protection filter 12 and the sensor unit 10 form part of the protective cassette 36. The protective cassette 36 further comprises an electronics unit 38. The electronics unit 38 is coupled with the sensor unit 16. The electronics unit 38 is provided to process the data of the sensor unit 16 and to control, depending on these, the glare-protection filter 12. The electronics unit 38 comprises for energy supply a battery and/or solar cell, which are/is not shown in detail (FIGS. 3, 7).

The optical glare-protection filter 12 is implemented by an electro-optical filter. The optical glare-protection filter 12 is implemented by an automatic darkening filter (ADF). The optical glare-protection filter 12 comprises a plurality of layers. The optical glare-protection filter 12 is embodied as a multi-layer composite. A number of layers is herein merely given as an example and may principally vary. Principally, it would also be conceivable that the optical glare-protection filter 12 is arranged additionally between transparent protective plates made, for example, of polycarbonate or glass, for additional protection of the optical glare-protection filter 12. A protective plate could in particular be used to protect the optical glare-protection filter 12 from sparks and other emissions of the welding process. Such a protective plate is herein in particular easily exchangeable by the user, in particular without using tools. The optical glare-protection filter 12 comprises a liquid-crystal layer, which serves as a screen of the glare-protection filter 12. The liquid-crystal layer is embodied by a translucent liquid-crystal display screen. The liquid-crystal layer is controlled by the electronics unit 38. The liquid-crystal layer of the glare-protection filter 12 is activated by the electronics unit 38 if a welding process or a flash of light is captured via the sensor unit 16. The liquid-crystal layer of the glare-protection filter 12 is darkened by the electronics unit 38 if a welding process or a flash of light is captured via the sensor unit 16. The liquid-crystal layer of the glare-protection filter 12 reduces the permeability for visible light through the glare-protection filter 12. The optical glare-protection filter 12 has in an active state, to give an example, a safety level regarding light permeability of at least 5 according to DIN (German Industrial Norm). Preferably the optical glare-protection filter 12 has in an active state, by way of example, a safety level range at least from 4 to 14 according to DIN. In a non-active state, the optical glare-protection filter 12 has, by way of example, a safety level regarding light permeability of 4 or less according to DIN. The liquid-crystal layer is arranged between two polarization layers of the glare-protection filter 12. The polarization layers are implemented by polarization foils (FIGS. 3, 7).

The glare-protection filter 12 has a rectangular base shape. A vertical extension 40 of the glare-protection filter 12 is herein, in a regular operative state, smaller than a horizontal extension 42 of the glare-protection filter 12. The vertical extension 40 of the glare-protection filter 12 is, as an example, 65 mm. The horizontal extension 42 of the glare-protection filter 12 is 132 mm. Principally, however, other extensions are conceivable which are deemed expedient by someone skilled in the art. The glare-protection filter 12 further comprises a nose cut-out 14. The nose cut-out 14 is implemented by an immaterial recess in a material portion of the glare-protection filter 12. The nose cut-out 14 is implemented by an immaterial recess in a material, at least partly translucent partial region of the glare-protection filter 12. The nose cut-out 14 is in an operative adjustment of the protection device 10 provided to partly accommodate a user's nose 30. In an operative adjustment, the glare-protection filter 12 partly encompasses the user's nose 30 in a region of the nose cut-out 14. The glare-protection filter 12 has a substantially rectangular base shape, wherein the nose-cutout 14 protrudes into the rectangular base shape. The nose cut-out 14 has a substantially triangular shape. The two sides delimited by the material portion of the glare-protection filter 12 include an angle of approximately 54 degrees with respect to each other. The two sides which are delimited by the material portion of the glare-protection filter 12 converge over a radius at their ends which face each other. The two sides delimited by the material portion of the glare-protection filter 12 converge at their ends, as an example, over an R9 radius. At their ends which face away from each other, the two sides delimited by the material portion of the glare-protection filter 12 extend towards the material portion of the glare-protection filter 12 with a radius. At their ends which face away from each other, the two sides delimited by the material portion of the glare-protection filter 12 extend towards the material portion of the glare-protection filter 12, as an example, with an R7 radius. The nose cut-out 14 extends from a lower edge, in particular from a center of the lower edge, of the glare-protection filter 12 towards a geometric center of the glare-protection filter 12. In a downward direction, the nose cut-out 14 is not delimited by the glare-protection filter 12. A shape of the nose cut-out 14 is adapted to a shape of a nose 30. A vertical extension 43 of the nose cut-out 14 is at least 45%, preferably at least 50% and especially preferentially at least 55% of a vertical extension 40 of the glare-protection filter 12. The vertical extension 43 of the nose cut-out 14 is approximately 57% of a vertical extension 40 of the glare-protection filter 12. The vertical extension 43 of the nose cut-out 14 is, as an example, 37 mm. Principally, however, another value of the extension 43 is also conceivable which is deemed expedient by someone skilled in the art (FIG. 7).

Figure 6:
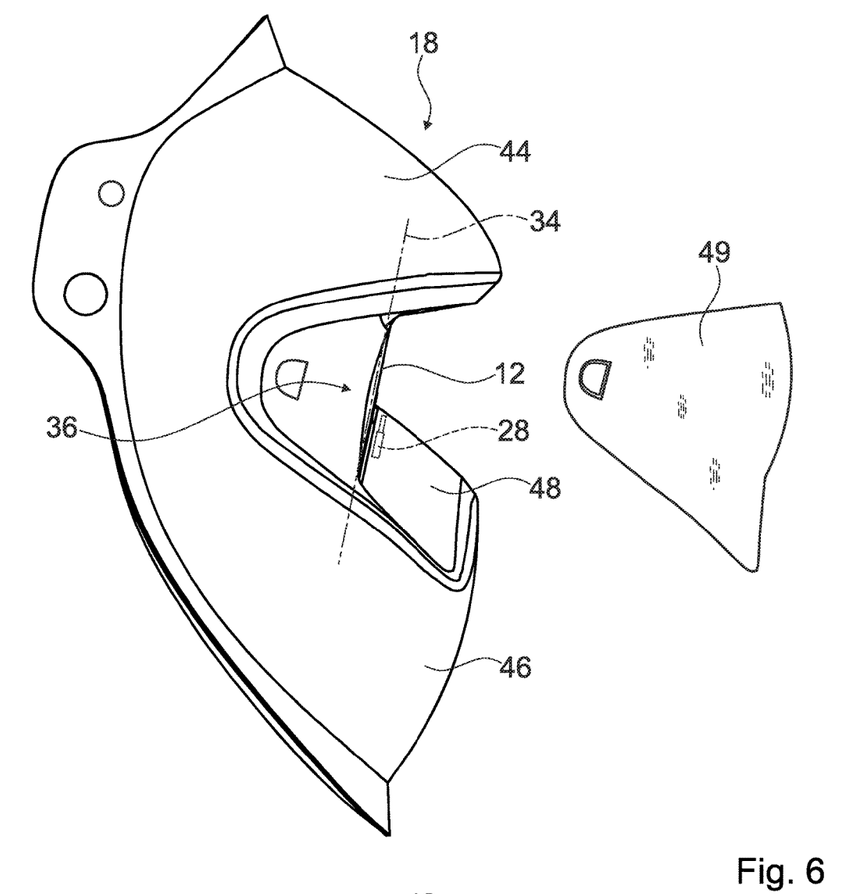

Furthermore the protection device 10 comprises a shield unit 18. The glare-protection filter 12 is fixedly accommodated in the shield unit 18. The glare-protection filter 12 is accommodated in the shield unit 18 fixedly as regards its position. The glare-protection filter 12 is fitted in a recess of the shield unit 18. The entire protective cassette 36 is fitted in a recess of the shield unit 18. The shield unit 18 is made of a substantially non-deformable material. The shield unit 18 is made of a plastic material, which is in particular resistant against sparks and/or other impacts that come with welding. The shield unit 18 is provided to cover and protect a user's face and/or head 22, in particular in accordance with the pertinent standards for welding masks. The shield unit 18 has a shape which is partly adapted to a head shape. In a worn state of the protection device 10, the shield unit 18 is partly bent around a user's face. In a worn state of the protection device 10, the shield unit 18 partly accommodates a user's face. The shield unit 18 comprises a forehead region 44, a chin region 46 and an eye region 48, which is arranged between the forehead region 44 and the chin region 46. The forehead region 44, the chin region 46 and the eye region 48 are embodied in a one-part implementation. The forehead region 44 and the chin region 46 have a substantially convex shape on an outer side which faces away from the user's face. The eye region 48 comprises a receptacle for accommodating the protective cassette 36. The eye region 48 is deepened towards the receptacle for the protective cassette 36. The receptacle for the protective cassette 36 is arranged offset inwards with respect to a base shape of the shield unit 18, and thus towards a user's face. The receptacle for the protective cassette 36 is arranged offset inwards with respect to the forehead region 44 and to the chin region 46 (FIG. 6).

Figure 2:
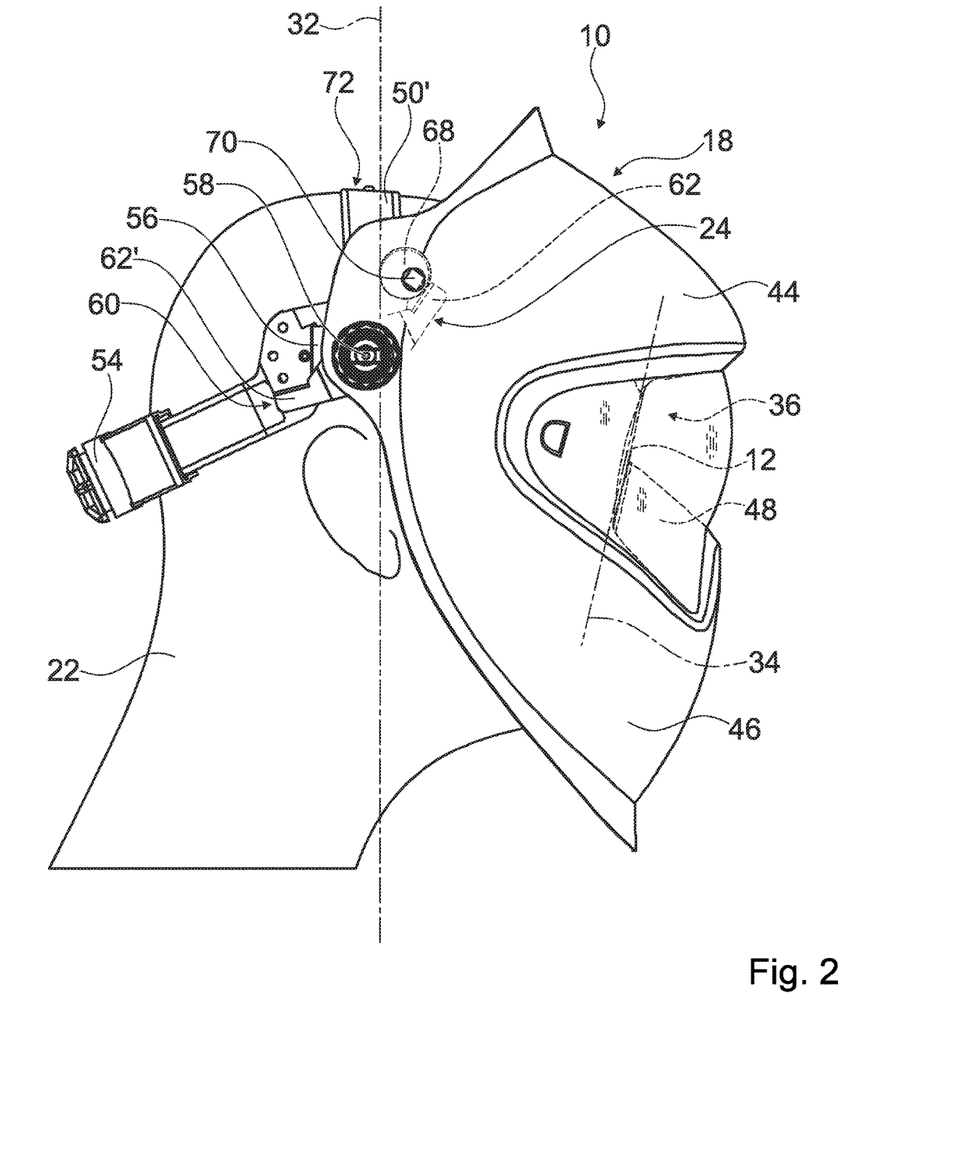

The protection device 10 further comprises a front cover plate 49. The front cover plate 49 is connected to the shield unit 18 via latch elements, which are not shown in detail. Preferably the front cover plate 49 comprises two latch recesses situated opposite each other, in each of which a latch element of the shield unit 18 engages in latch fashion. Due to the latching, the front cover plate 49 is easily demountable. This allows easy cleaning and/or easy replacement. The front cover plate 49 is embodied transparent. The front cover plate 49 is provided for a protection of the protective cassette 36. The front cover plate 49 screens the protective cassette 36 off from an outside. In this way damaging of the protective cassette 36 is avoidable. In case of the front cover plate 49 being damaged, it is easily and cost-effectively replaceable, in particular in contrast to the protective cassette 36. The front cover plate 49 screens off a substantial portion of the eye region 48 of the shield unit 18. The front cover plate 49 is situated entirely lying upon the shield unit 18 on a circumferential edge. Principally it is conceivable that a sealing is provided at the shield unit 18 and/or at the front cover plate 49, preventing, for example, dust and/or sparks from entering an interspace between the protective cassette 36 and the front cover plate 49. The front cover plate 49 substantially screens off the deepening of the eye region 48. The front cover plate 49 is bent corresponding to a base shape of the shield unit 18 (FIGS. 2, 6).

Figure 4:
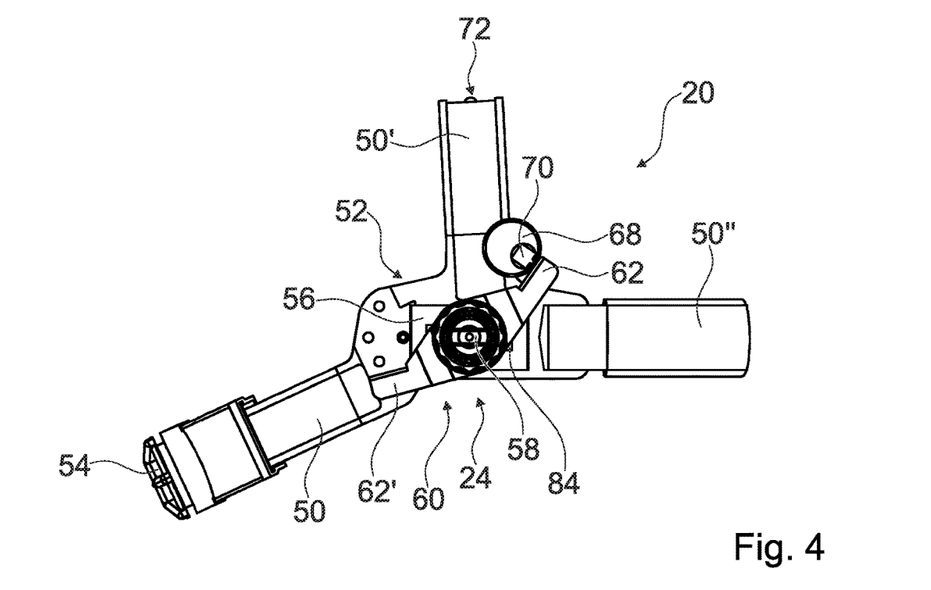
Figure 5:
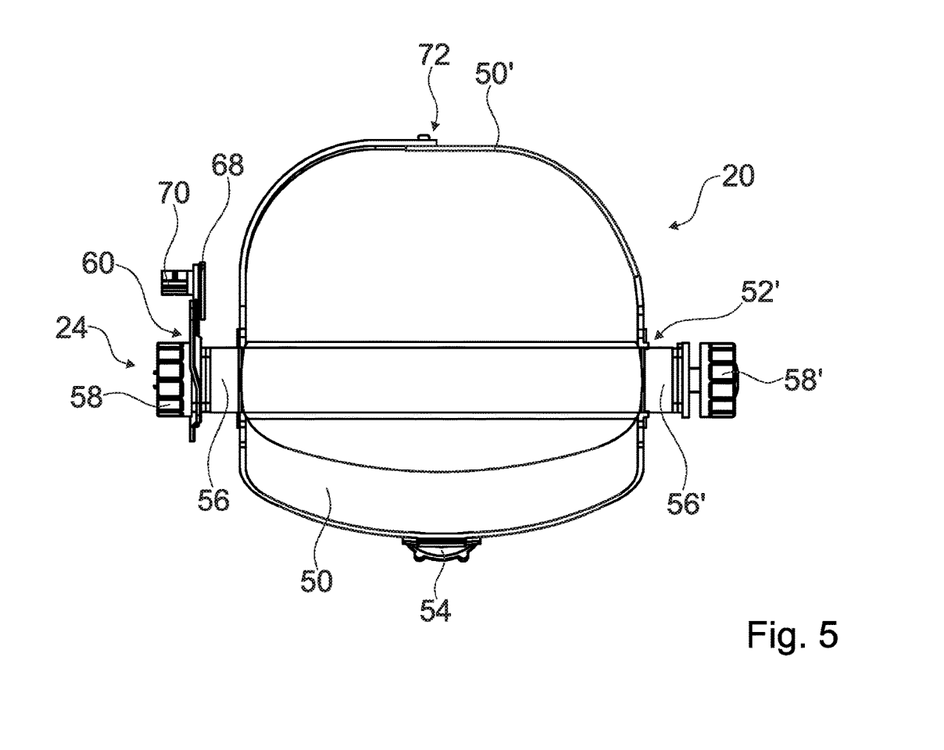

The protection device 10 further comprises a head-fastening unit 20. The head-fastening unit 20 is provided for a fastening to the user's head 22. The head-fastening unit 20 is embodied by a head strap. The head-fastening unit 20 comprises a plurality of head strap elements 50, 50', 50", which are respectively provided to at least partly extend around the user's head 22. The head-fastening unit 20 comprises three head strap elements 50, 50', 50", which are respectively provided to extend around the user's head 22 in different planes. The three head strap elements 50, 50', 50" are embodied band-shaped. A first head strap element 50 extends from a first common connection point 52 above a user's ear around a back of the user's head 22 to a second common connection point 52' above the other ear of the user. An effective length of the first head strap element 50 is adjustable. The head-fastening unit 20 comprises an adjusting element 54 at the head strap element 50. The adjusting element 54 is embodied by an adjusting wheel, which is, for example, known from helmets and via which an effective length of the first head strap element 50 is adjustable by rotation. A second head strap element 50' extends from the first common connection point 52 across an upper head of the user's head 22 to the second common connection point 52' above the other ear of the user. The second head strap element 50' extends from the first common connection point 52 in an angle of approximately 120 degrees with respect to the first head strap element 50. An effective length of the second head strap element 50' is adjustable. For this purpose, the second head strap element 50' is embodied in a two-part implementation. The two parts of the second head strap element 50' are connected via an adjustable closure unit 72. The adjustable closure unit 72 is implemented by a snapback closure. A third head strap element 50" extends from the first common connection point 52 about a forehead of the user's head 22 to the second common connection point 52' above the other ear of the user. The third head strap element 50" extends from the first common connection point 52 in an angle of approximately 90 degrees with respect to the second head strap element 50'. The three head strap elements 50, 50', 50" of the head-fastening unit 20 are firmly connected to each other via the connection points 52, 52'. The head-fastening unit 20 is made of a partially elastic plastic material. Principally, however, another material deemed expedient by someone skilled in the art would also be conceivable (FIGS. 2, 4, 5).

The head-fastening unit 20 defines, in a regularly worn state, a head axis 32. The head axis 32 is rigid with respect to the user's head 22. The head axis 32 describes a position and orientation of the head 22. The head axis 32 extends through a geometric center of the user's head 22. Furthermore, the head axis 32 extends, in case of an upright posture of the user, in parallel to a main extension direction of the user's rump. The head axis 32 moreover extends at least approximately in parallel to an extension plane of the second head strap element 50' (FIGS. 2, 3).

The protection device 10 further comprises an adjusting unit 24. A position of the shield unit 18 is implemented in such a way that it is movable in a defined manner with respect to the head-fastening unit 20 by the adjusting unit 24. By means of the adjusting unit 24, a position of the shield unit 18 is adjustable with respect to the head-fastening unit 20 in a defined manner. A position of the shield unit 18 is implemented in such a way that it is fixable in at least two adjustments with respect to the at least one head-fastening unit 20 by means of the adjusting unit 24. A position of the shield unit 18 is implemented in such a way that it is fixable in at least two operative adjustments with respect to the at least one head-fastening unit 20 by means of the adjusting unit 24. A position of the shield unit 18 is implemented in such a way that it is fixable, in a limited range, in any desired operative adjustment with respect to the at least one head-fastening unit 20 by means of the adjusting unit 24. By means of the adjusting unit 24, a position and orientation of the shield unit 18 in an operative adjustment may be chosen freely, wherein the position and orientation of the shield unit 18 is fixable. The shield unit 18 is connected to the head-fastening unit 20 via the adjusting unit 24. The adjusting unit 24 is connected to the head-fastening unit 20 in the two connection points 52, 52'. The adjusting unit 24 is furthermore connected to the shield unit 18 in a peripheral region of the forehead region 44 of the shield unit 18. The adjusting unit 24 comprises a base element 56. The base element 56 is fixedly connected to the head-fastening unit 20 in the first connection point 52 of the head-fastening unit 20. The adjusting unit 24 furthermore comprises a second base element 56', which is mirror-symmetrical to the base element 56. The second base element 56' is fixedly connected to the head-fastening unit 20 in the second connection point 52' of the head-fastening unit 20 (FIG. 2).

Figure 8:
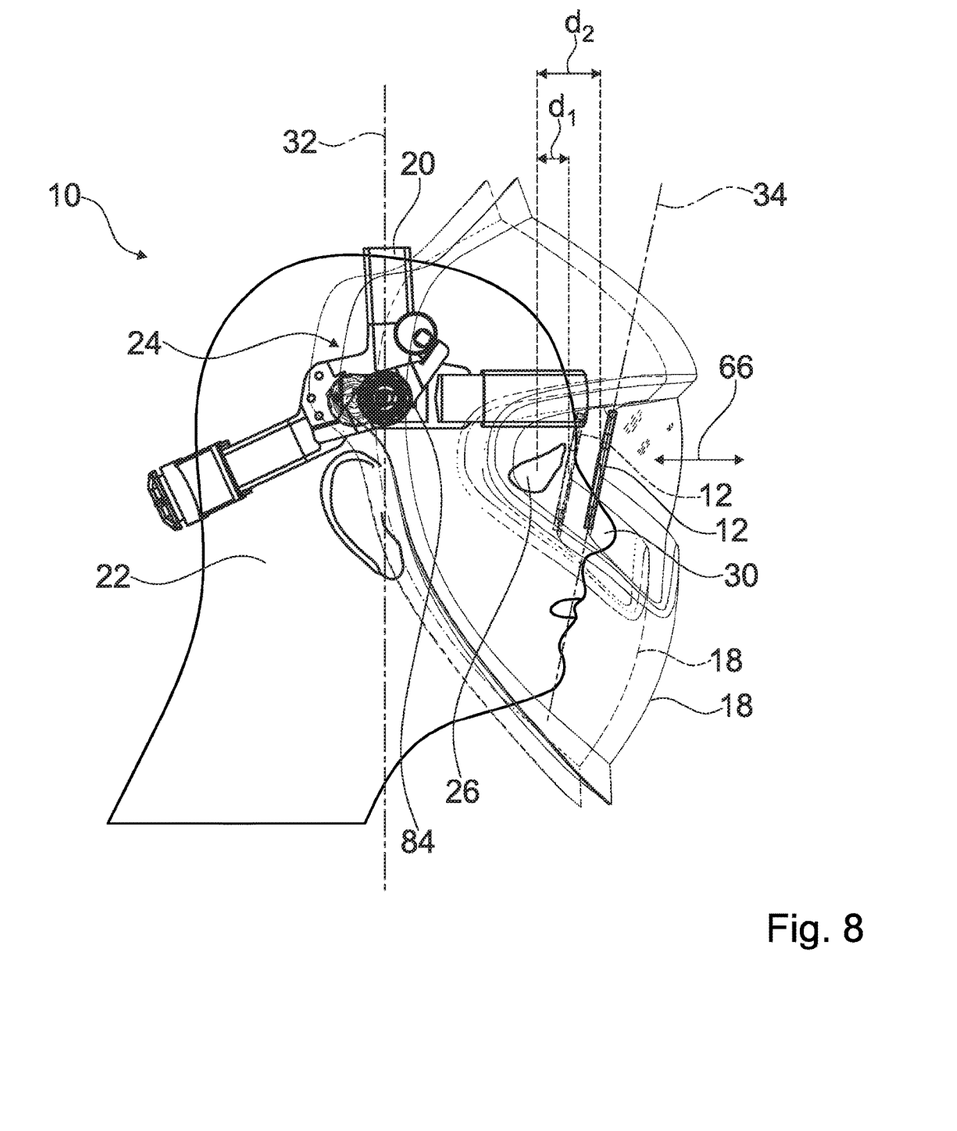

The adjusting unit 24 further comprises a rotary wheel 58, which is rotatably supported on the shield unit 18. The rotary wheel 58 is furthermore translationally guided in a guiding rail 84 of the first base element 56. The rotary wheel 58 is guided in the guiding rail 84 of the first base element 56 perpendicularly to the head axis 32. In the guiding rail 84 of the first base element 56 a guiding element is guided (not shown in detail), on which the rotary wheel 58 is arranged. The guiding element is implemented by a square nut which the rotary wheel 58 is screwed into. A position of the rotary wheel 58 with respect to the guiding rail 84 of the base element 56 may be fixed or released by a user via turning. In a released state, the rotary wheel 58 is displaceable in the guiding rail 84. On a side that is situated opposite the rotary wheel 58, an identical second rotary wheel 58' is arranged, which is correspondingly translationally guided in a guiding rail of the second base element 56'. A direct distance d1, d2 between the user's eyes 26 and the optical glare-protection filter 12 is implemented in such a way that it is adjustable by the adjusting unit 24. A direct distance d1, d2 between the user's eyes 26 and the optical glare-protection filter 12 is adjustable by the adjusting unit 24 in a horizontal direction, respectively perpendicularly to the head axis 32. The direct distance d1, d2 between the user's eyes 26 and the optical glare-protection filter 12 can be modified via the rotary wheels 58, 58' of the adjusting unit 24. Via the rotary wheels 58, 58' a position of the shield unit 18 can be modified with respect to the user's face in a longitudinal direction 66. If a desired longitudinal position has been found, the position may be fixed via turning the rotary wheels 58, 58'. Depending on a welder's head circumference and well-being, the longitudinal position of the protective cassette 36 is advantageously adjustable in this way. In particular, this allows an optimum adaption of a longitudinal position of the protective cassette 36 for spectacle wearers as well. The nearer the protective cassette 36 is arranged to the face, the greater will the field of vision 74 be for the user. Furthermore, the rotary wheels 58, 58' form a rotary joint of the shield unit 18. The shield unit 18 is rotatably supported at the rotary wheels 58, 58'. Via the rotary wheels 58, 58', the shield unit 18 is pivotable upwards. In this way the shield unit 18 is removable out of a region of the face of the user's head 22 without taking off the protection device 10. In FIG. 8 two different distances d1, d2 between the user's eyes 26 and the optical glare-protection filter 12 are exemplarily shown, which are adjustable via the adjusting unit 24. Stepless adjustment of the distance d1, d2 between the user's eyes 26 and the optical glare-protection filter 12 is possible (FIGS. 2, 4, 8).

Figure 9:
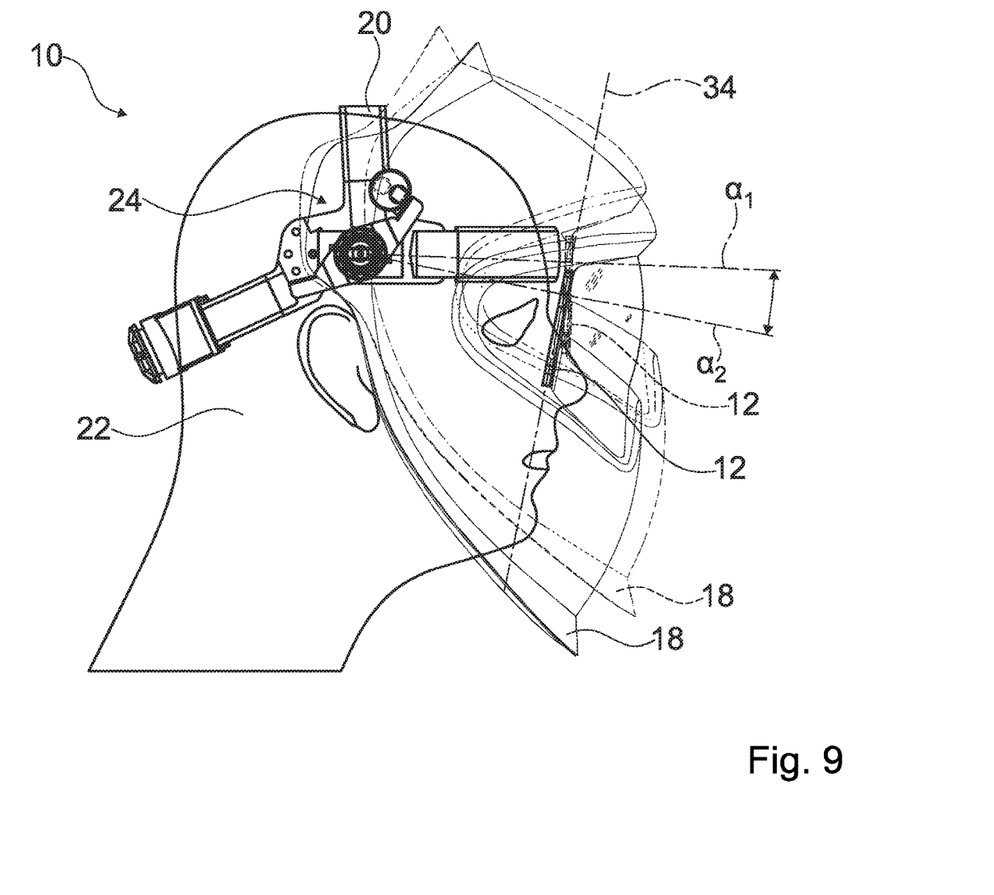

Furthermore, in an operative adjustment an angle $\alpha 1$, $\alpha 2$ of the shield unit 18 is implemented in such a way that it is adjustable with respect to the head-fastening unit 20. For this purpose the adjusting unit 24 comprises a lever 60. The lever 60 is fixedly connected to the guiding element guided in the guiding rail 84 of the first base element 56. The lever 60 is fixedly connected to the square nut which the rotary wheel 58 is screwed into. The lever 60 thus has a fix angle position with respect to the head-fastening unit 20. The lever 60 comprises two lever arms 62, 62', which are arranged on opposite sides of a rotary axis of the rotary wheel 58. The lever arms 62, 62' each form a stop. The lever arms 62, 62' each extend in a plane in parallel to the head axis 32 and perpendicularly to a main extension plane 34 of the optical glare-protection filter 12. A first lever arm 62 extends from the pivot axis in a direction towards the optical glare-protection filter 12. The first lever arm 62 comprises a corresponding stop. The corresponding stop is embodied by an eccentrically supported disk 68. The eccentrically supported disk 68 is embodied circular. The eccentrically supported disk 68 is supported on the shield unit 18 in such a way that it is rotatable via an adjusting wheel 70. The adjusting wheel 70 is arranged on the shield unit 18 above the rotary wheel 58. On the shield unit 18 a crown gear is arranged around the adjusting wheel 70 on an inner side, via which crown gear the adjusting wheel 70 is latched in the respective adjustment positions. This allows avoiding undesired adjusting of the adjusting wheel 70. Moreover an acoustical feedback may be given with adjusting. Via the adjusting wheel 70 an angle $\alpha 1$, $\alpha 2$ of the shield unit 18 is in an operative position adjustable with respect to the head-fastening unit 20. Via the adjusting wheel 70, an angle of the optical glare-protection filter 12 may be adjusted with respect to the head axis 32. Depending on a rotary position of the adjusting wheel 70, the first lever arm 62 lies upon different points of a circumference of the disk 68. Depending on a point of the circumference of the disk 68 which the first lever arm 62 lies upon, a distance between the lever arm 62' and a rotary axis of the disk 68 changes due to the eccentricity of the disk 68. As a result of this, an angle between the shield unit 18 and the lever 60 is changed. The lever 60 has a fix angle position with respect to the head-fastening unit 20. This results in a change of the angle $\alpha 1$, $\alpha 2$ of the shield unit 18 with respect to the head-fastening unit 20. The disk 68 is pressed against the first lever arm 62 of the lever 60 by a weight of the shield unit 18. In this way an angle of the optical glare-protection filter 12 may be adapted to the respective shape of a user's face. In a respective stop position, the shield unit 18 is in an operative position. A second lever arm 62' extends from the pivot axis in a direction facing away from the optical glare-protection filter 12. The second lever arm 62' comprises a corresponding stop. The corresponding stop is also embodied by the eccentrically supported disk 68. The second lever arm 62' forms a stop of the shield unit 18 in a state in which the shield unit 18 has been pivoted upwards and is arranged removed out of a region of the face of the user's head 22. In a state when the shield unit 18 has been pivoted upwards, the disk 68 is also pressed against the second lever arm 62' of the lever 60 by a weight of the shield unit 18. In a respective stop position, the shield unit 18 is in a rest position. In FIG. 9 two different angles α1, α2 of the shield unit 18 are shown by way of example, which are adjustable by means of the adjusting unit 24. A stepless adjustment of the angle α1, α2 of the shield unit 18 is possible. In FIG. 9 two different angles α1, α2 of the shield unit 18 are shown by way of example, which are adjustable in an operative position by means of the adjusting unit 24 (FIGS. 2, 4, 9).

The main extension plane 34 of the optical glare-protection filter 12 is in at least one operative adjustment substantially angled with respect to the head axis 32. In case of a maximum angle position of the shield unit 18 with respect to the head-fastening unit 20 with the angle $\alpha_1$, the main extension plane 34 of the optical glare-protection filter 12 is substantially angled with respect to the head axis 32. A smallest angle between the main extension plane 34 of the optical glare-protection filter 12 and the head axis 32 is in the maximum angle position of the shield unit 18 at least 5°, preferably at least 10°. The smallest angle is approximately 15°. The main extension plane 34 of the optical glare-protection filter 12 is in this case angled with respect to the head axis 32 in such a way that a lower edge of the optical glare-protection filter 12, in which the nose cut-out 14 is arranged, is located nearer to the head axis 32 than an upper edge of the optical glare-protection filter 12. Angling the optical glare-protection filter 12 allows a user's perpendicular view through the optical glare-protection filter 12, thus reducing the impact the dependency of the optical glare-protection filter 12 on a viewing angle has onto the viewing quality (FIG. 9).

Figure 10:
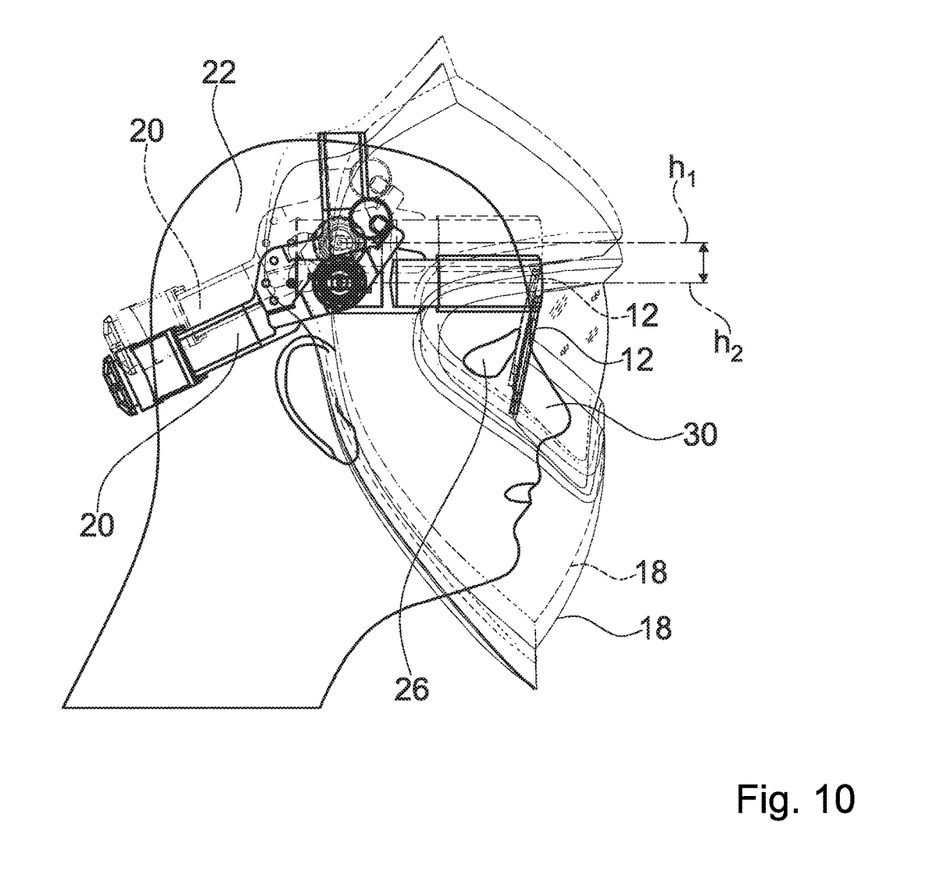

Furthermore, a height $h_1$, $h_2$ of the shield unit 18 is implemented in such a way that it is in an operative adjustment adjustable with respect to the head-fastening unit 20. A height $h_1$, $h_2$ of the shield unit 18 is implemented in such a way that it is in an operative adjustment adjustable, by means of the adjusting unit 24, in parallel to the head axis 32 with respect to the user's head 22. For this purpose the adjusting unit 24 comprises the adjustable closure unit 72. The adjustable closure unit 72 is configured to connect the two parts of the second head strap element 50'. The adjustable closure unit 72 is implemented by a snapback closure. The adjustable closure unit 72 is embodied in a one-part implementation with the second head strap element 50'. By means of the adjustable closure unit 72 an effective length of the second head strap element 50' may be changed. By means of the adjustable closure unit 72 an effective length of the second head strap element 50' may be changed manually by the user. As a result of the change in the effective length of the second head strap element 50', a height of the connection points 52, 52' is adjustable in parallel to the head axis 32 with respect to the user's head 22. And this allows adjusting the height level $h_1$, $h_2$ of the shield unit 18. In FIG. 10 two different heights $h_1$, $h_2$ of the shield unit 18 are shown, to give an example, which are adjustable via the adjusting unit 24. In this a number of adjustable heights $h_1$, $h_2$ depends on an implementation of the adjustable closure unit 72. Principally, however, a stepless adjustability of the closure unit 72 and hence of the height $h_1$, $h_2$ would also be conceivable (FIGS. 2, 4, 10).

The shield unit 18 further comprises a face abutment 28. The face abutment 28 is provided to contact a user's face in an end position of the shield unit 18. An abutment position is herein defined by a contact of face and face abutment 28. An abutment position herein defines an operative adjustment. The face abutment 28 of the shield unit 18 is provided for positioning the shield unit 18 with respect to a user's face. The face abutment 28 is embodied by a nosepiece. The face abutment 28 is embodied by a spectacle-like nosepiece. The face abutment 28 is in an operative adjustment configured to contact a user's nose 30. The face abutment 28 is in an operative adjustment configured to contact a nose bridge of the user's nose 30. The face abutment 28 comprises two nose pads, which are in an operative position provided to respectively contact one side of the nose 30. A position and orientation of the nose pads of the face abutment 28 is adjustable. The nose pads of the face abutment 28 are for this purpose connected to a base body of the shield unit 18 via deformable connecting webs. The face abutment 28 is thus adaptable to a shape of a nose 30. This allows reliably defining an end position of the shield unit 18. As a result of this, in particular a reliable positioning of the shield unit 18 with respect to the user's eyes 26 is achievable. The face abutment 28 is arranged in a region of the nose cut-out 14 of the optical glare-protection filter 12. Principally, however, another implementation and/or arrangement of the face abutment 28 deemed expedient by someone skilled in the art would also be conceivable (FIG. 3).

Figure 11:
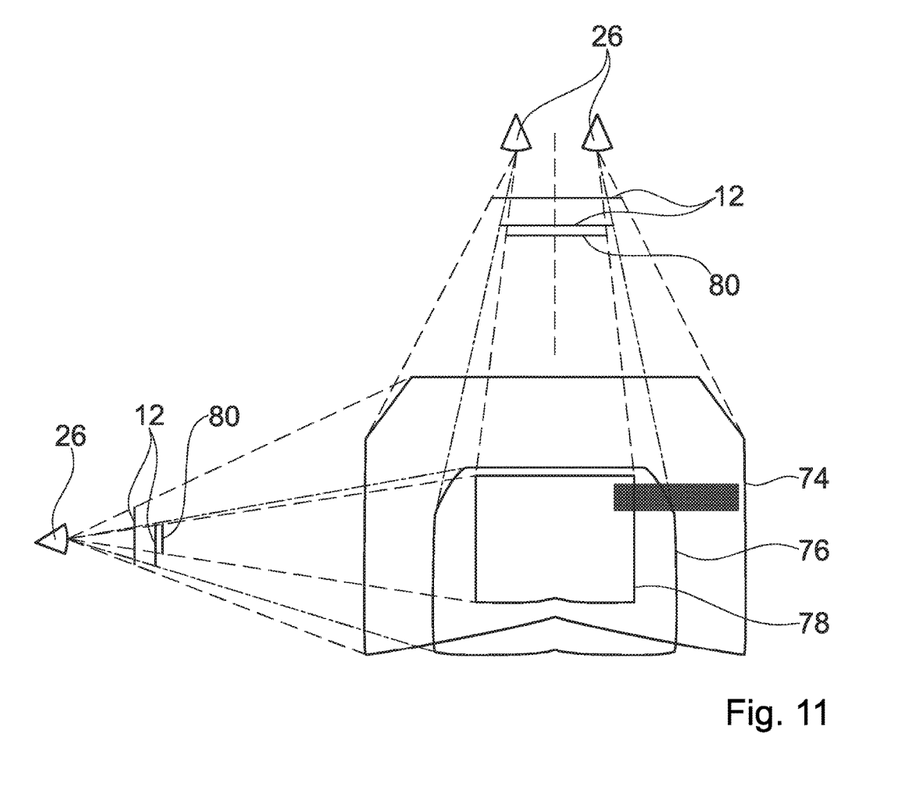
Figure 12:
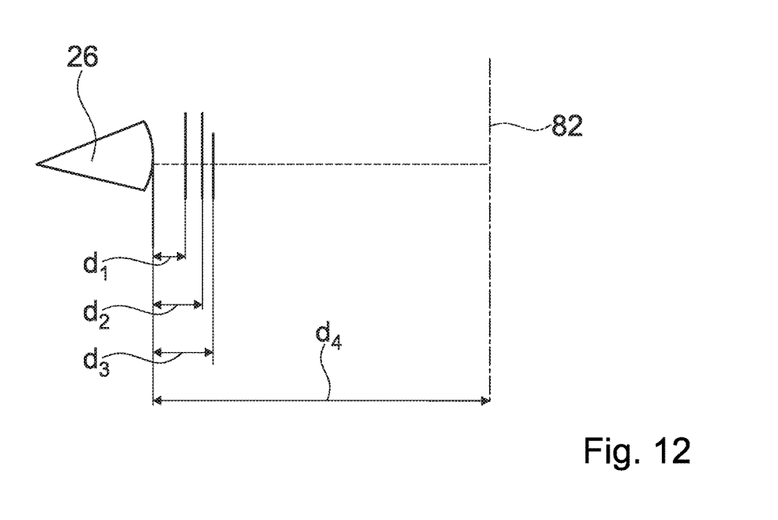

FIG. 11 shows two possible fields of vision 74, 76 of the protection device 10 in two different adjustments in comparison to the field of vision 78 of already known welding helmets, here as an example the field of vision 78 of a welding helmet of Optrel AG with the denomination "e684". An optical glare-protection filter 80 of the welding helmet denominated "e684" has a rectangular standard size of 50 mm×100 mm. The optical glare-protection filter 80 of the welding helmet denominated "e684" hence has an area of 50 $cm^2$. The optical glare-protection filter 80 of the protection device 10 has an area of approximately 71 $cm^2$. Herein the fields of vision 74, 76, 78 are measured in a plane 82 in parallel to the glare-protection filters 12, 80 and at a distance of 600 mm to an eyeball of a user of the protection device 10 respectively of the welding helmet with the denomination "e684" (FIG. 12). Stereo vision is measured. The first field of vision 74 of the protection device 10 has in a first adjustment, in the plane 82, an area of 6946 $cm^2$. In the first adjustment of the protection device 10 the optical glare-protection filter 12 is set to a minimum distance $d_1$ to the user's eyes by means of the adjusting unit 24. The distance $d_1$ is approximately 20 mm. The second field of vision 76 of the protection device 10 in a second adjustment has an area of 2525 $cm^2$ in the plane 82. In the second adjustment of the protection device 10 the optical glare-protection filter 12 is set to a maximum distance $d_2$ to the user's eyes by means of the adjusting unit 24. The distance $d_2$ is approximately 40 mm. The field of vision 78 of the welding helmet denominated "e684" has, in a regularly worn state, an area of 1090 cm2 in the plane 82. The field of vision 78 of the welding helmet denominated "e684" features, in a regularly worn state, a distance $d_3$ of approximately 50 mm to the user's eyes. The field of vision 74, 76 of the protection device 10 in the plane 82 is thus greater than the field of vision 78 of the already known welding helmet by at least 200%, preferably in at least one adjustment by at least 400% and especially preferentially in at least one adjustment, in particular an optimum adjustment, by at least 600%. Furthermore, with respect to a size of the optical glare-protection filters 12, 80, the field of vision 74, 76 of the protection device 10 in the plane 82 is greater than the field of vision 78 of the already known welding helmet by at least 150%, preferably in at least one adjustment by at least 250% and particularly preferably in at least one adjustment by at least 500% The area of the field of vision 74, 76 of the protection device 10 in the plane 82 is twice as great, preferably at least three times as great in at least one adjustment and particularly preferably in at least one adjustment, in particular an optimum adjustment, at least five times as great than an area of the optical glare-protection filter 12 of the protection device 10.

The invention claimed is:

1. A protection device, in particular, a glare-protection device comprising:
    at least one optical glare-protection filter including a nose cut-out;
    at least one sensor unit, which is provided to capture a work state and to control, depending on the work state, a permeability of the glare-protection filter;
    at least one shield unit, in which the at least one glare-protection filter is fixedly accommodated;
    at least one head-fastening unit for a fastening to a user's head; and
    at least one adjusting unit, by which a position of the at least one shield unit is movable with respect to the at least one head-fastening unit in a defined manner, wherein
    a direct distance between the user's eyes and the optical glare-protection filter is adjustable by the at least one adjusting unit,
    the adjusting unit includes a base element and a rotary wheel, wherein the rotary wheel is translationally guided in a guiding rail of the base element,
    the distance between the user's eyes and the optical glare-protection filter is steplessly adjustable,
    the position of the at least one shield unit is implemented in such a way that it is fixable by the at least one adjusting unit in at least two fixable operative adjustments,
    the at least two fixable operative adjustments chosen from differing the direct distance between the optical glare-protection filter and the user's eyes and/or differing an angle between the shield unit and the head-fastening unit, and/or by a height level at which the optical glare-protection filter is arranged with respect to the user's head, and
    the user can choose whether the shield unit is to lie upon a user's nose or is to be spaced apart from the user's nose when in an operative position.

2. The protection device according to claim 1, wherein a height of the at least one shield unit is, in an operative adjustment, adjustable by means of the at least one adjusting unit with respect to the at least one head-fastening unit.

3. The protection device according to claim 1, wherein the at least one shield unit comprises at least one face abutment, which is provided to contact a user's face if the user chooses to have the shield unit lie upon the user's nose.

4. The protection device according to claim 3, wherein the at least one face abutment is embodied by a nosepiece, which is, in at least one operative adjustment, provided to contact a user's nose.

5. The protection device according to claim 4, wherein the at least one face abutment of the at least one shield unit is provided for a positioning of the at least one shield unit with respect to a user's face.

6. The protection device according to claim 1, wherein the head-fastening unit defines, in a regularly worn state, a head axis, with respect to which a main extension plane of the optical glare-protection filter is substantially angled in at least one operative adjustment.

7. The protection device according to claim 1, wherein the at least one head-fastening unit is embodied by a head strap.

8. The protection device according to claim 1, wherein the at least one shield unit is made of an at least substantially non-deformable material.

9. The protection device according to claim 1, wherein the adjusting unit includes a lever having two lever arms each forming a stop, wherein the corresponding stop is embodied by an eccentrically supported disk, which is supported on the shield unit in such a way that it is rotatable via an adjusting wheel.

* * * * *